(12) United States Patent
Bayon et al.

(10) Patent No.: US 8,962,006 B2
(45) Date of Patent: Feb. 24, 2015

(54) COMPOSITE MESH INCLUDING A 3D MESH AND A NON POROUS FILM OF OXIDIZED CELLULOSE FROM BACTERIAL CELLULOSE ORIGIN

(75) Inventors: Yves Bayon, Lyons (FR); Sébastien Ladet, Lyons (FR); Olivier Lefranc, Chatillon sur Chalaronne (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 350 days.

(21) Appl. No.: 13/125,655

(22) PCT Filed: Nov. 6, 2009

(86) PCT No.: PCT/IB2009/007666
§ 371 (c)(1),
(2), (4) Date: Jul. 18, 2011

(87) PCT Pub. No.: WO2010/052585
PCT Pub. Date: May 14, 2010

(65) Prior Publication Data
US 2011/0264120 A1    Oct. 27, 2011

Related U.S. Application Data

(60) Provisional application No. 61/112,292, filed on Nov. 7, 2008.

(51) Int. Cl.
| | | |
|---|---|---|
| *A61B 17/00* | (2006.01) | |
| *C12P 19/04* | (2006.01) | |
| *B32B 37/06* | (2006.01) | |
| *B32B 37/16* | (2006.01) | |
| *B32B 37/04* | (2006.01) | |
| *A61L 27/58* | (2006.01) | |
| *A61L 27/20* | (2006.01) | |

(52) U.S. Cl.
CPC ...... *A61L 27/58* (2013.01); *A61L 27/20* (2013.01)
USPC .......... 424/422; 606/151; 156/60; 156/308.2; 156/272.8; 435/101

(58) Field of Classification Search
None
See application file for complete search history.

(56) References Cited

U.S. PATENT DOCUMENTS

| 6,451,032 B1 * | 9/2002 | Ory et al. ............... 606/151 |
| 2006/0147612 A1 | 7/2006 | Da Rocha Loures |
| 2007/0213522 A1 * | 9/2007 | Harris et al. ............. 536/56 |

FOREIGN PATENT DOCUMENTS

| EP | 0 396 344 | * 11/1990 |
| WO | WO 2006/042287 | * 4/2006 |

OTHER PUBLICATIONS

International Search Report PCT/IB2009/007666 dated Sep. 14, 2010.

* cited by examiner

*Primary Examiner* — Robert A Wax
*Assistant Examiner* — Danah Al-Awadi

(57) ABSTRACT

The present invention relates to a composite implant comprising: a prosthetic fabric having a first side and a second side, a non-porous film of bacterial cellulose secured to the first side of the fabric. The invention further relates to a method of making such an implant.

9 Claims, 2 Drawing Sheets

COMPOSITE MESH INCLUDING A 3D MESH AND A NON POROUS FILM OF OXIDIZED CELLULOSE FROM BACTERIAL CELLULOSE ORIGIN

CROSS-REFERENCE TO RELATED APPLICATIONS

This application is a U.S. National Stage Application filed under 35 U.S.C. §371(a) of International Application No. PCT/IB2009/007666 filed Nov. 6, 2009, which claims the benefit of and priority to U.S. Provisional Application Ser. No. 61/112,292 filed Nov. 7, 2008, the entire contents of which are incorporated by reference herein.

Composite implants include a prosthetic fabric and a bioresorbable film of oxidized cellulose from microbial cellulose origin.

An aspect of the present invention is a composite implant comprising:
 a prosthetic fabric having a first side and a second side,
 a non-porous film of bacterial cellulose secured to the first side of the fabric.

The non-porous film of bacterial cellulose may be oxidized. The non-porous film of bacterial cellulose may be derived from *Acetobacter xylinum*.

The prosthetic fabric may comprise a three-dimensional knit.

In embodiments, the prosthetic fabric has a thickness and the non-porous film of bacterial cellulose penetrates into the prosthetic fabric to a depth of less than 50% of the thickness of the prosthetic fabric.

Another aspect of the present invention is a method of making a composite implant comprising:
 providing a prosthetic fabric having a first side and a second side; and
 securing a film of bacterial cellulose to the first side of the prosthetic fabric.

In embodiments, securing a film of bacterial cellulose to the first side of the prosthetic fabric comprises:
 contacting the prosthetic fabric with a culture of cellulose-producing bacteria; and
 culturing cellulose-producing bacteria.

In embodiments, securing a film of bacterial cellulose to the first side of the prosthetic fabric comprises:
 contacting the prosthetic fabric with a film of bacterial cellulose which has been at least partially melted.

In embodiments, the film of bacterial cellulose has been at least partially melted using infrared light or thermal or ultraviolet lasers.

In embodiments, the method further comprises applying mechanical pressure to the prosthetic fabric while in contact with the film of bacterial cellulose.

Another aspect of the present invention is a method of treating a wound comprising contacting a wound with a composite implant as described above.

Figure 1A:
Figure 1B:
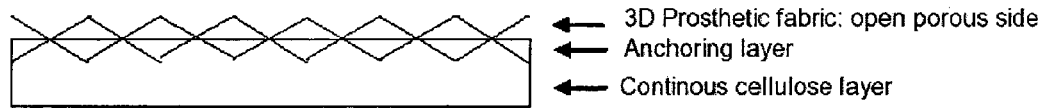
Figure 2A:
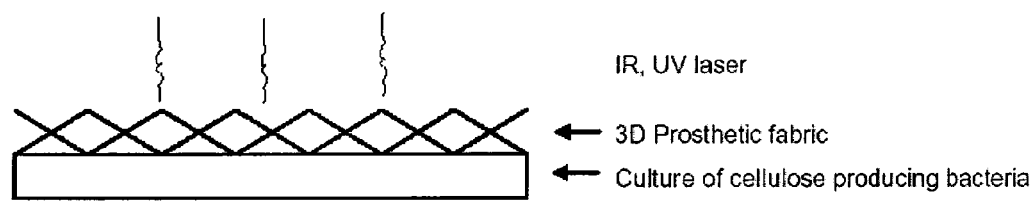
Figure 2B:
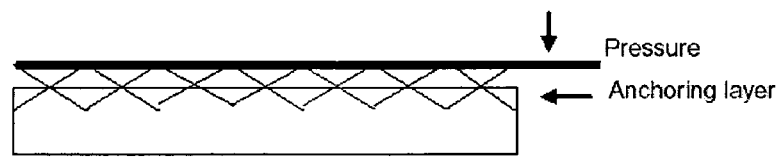

Various embodiments of the composite implant are described herein with reference to the drawings wherein:

FIGS. 1A and 1B are schematic cross-sectional views of a composite implant described in at least one of the embodiments provided in the present disclosure; and, FIGS. 2A and 2B are schematic cross-sectional views of a composite implant described in at least another one of the embodiments provided in the present disclosure.

The prosthetic fabric has a three dimensional ("3D") structure having two faces. One face is porous and open to post surgical cell colonization. The second face is bound to a non porous film of oxidized cellulose from microbial cellulose origin. The cellulose film can be a uniform coating coextensive with and covering one entire surface of the fabric. In embodiments, the cellulose film can be present in some other coating pattern to fulfill the expectations for the use of the implant. A continuous film prevents inflammatory exudates from crossing through the fabric, thereby preventing formation of tissular adhesions to the fabric. The resorption of the film can be tailored by adjusting the degree to which the cellulose is oxidized.

In the present disclosure, the term "implant" is intended to mean a biocompatible medical implant that can be implanted in the human or animal body.

In the present disclosure, the term "bioresorbable" is intended to mean the characteristic according to which an implant and/or a material is degraded by the biological tissues and the surrounding fluids, in vivo after a given period of time, that may vary, for example, from one day to several months, depending on the chemical nature of the implant and/or of the material.

For the purpose of the present disclosure, the term "porous" is intended to mean the characteristic according to which a structure exhibits pores, or alternatively gaps, alveoli, holes or orifices, which are open, which may or may not be evenly distributed, and which promote all cell colonization.

For the purpose of the present disclosure, the term "continuous" is intended to mean the characteristic to which structure extends without any break, or interruption, and which prevents formation of fibrinous structure between prosthetic fabric and surrounding tissue of the body, thereby acting as an adhesion barrier and preventing the formation of unwanted scar tissue. It may be as well a physical barrier against microbial contamination.

In the present disclosure, the microbial cellulose as wet pellicles or films may be produced from bacteria that synthesize cellulose. Cellulose is synthesized by bacteria belonging to the genera *Acetobacter, Rhizobium, Agrobacterium*, and *Sarcina*. Cellulose can be produced by certain bacteria from glucose in the presence of oxygen, (such as, for example, *Acetobacter xylinum*, referenced hereinafter as the "bacteria"), in static conditions or in a bioreactor (see, e.g. U.S. Pat. Nos. 4,912,049 and 5,955,326, the entire disclosures of which are incorporated herein by this reference). Cellulose suitable for use in the present implants can be obtained by the fermentation of the bacteria. In embodiments, a derivative of the cellulose is employed, such as oxidized cellulose resulting from the oxidation of the cellulose by periodic acid or nitrogen dioxide.

Microbial cellulose possesses inherent characteristics which allow effective promotion of wound healing as described earlier (see, e.g. U.S. Pat. No. 7,390,492, the entire disclosures of which are incorporated herein by this reference). In this regard, microbial cellulose displays properties that distinguish it from plant cellulose and other natural polymeric materials, such as unique multi-layer three dimensional laminar structures. In this regard, microbial cellulose shows excellent wet strength, does not easily breakdown under compression and demonstrates high moisture handling ability.

In the present disclosure the prosthetic fabric may be produced from fibers of any biocompatible polymer using techniques know to those skilled in the art, such as knitting, weaving, tatting, knipling or the like. It is envisioned that the prosthetic fabric may be formed from any permanent biocompatible materials (e.g. polyesters, polypropylene), biodegradable biocompatible materials (e.g. polylactic acid, polyglycolic acid, oxidized cellulose) or with a combination at any proportion of both permanent and biodegradable materials. The prosthetic fabric may, for example, have an openwork three-dimensional ("3D") structure (see, e.g. U.S. Pat. No. 6,451,032, the entire disclosures of which are incorporated herein by this reference), and in particular a "honeycomb" structure, and thus a certain thickness which separates the two surfaces of the fabric. This fabric can be obtained, for example, with a Rachel knit formed on a double needlebed. The spacing of the two needle beds and the delivery speeds of the yarns allow a finished fabric to be obtained in three dimensions (three-dimensional structure), with a thickness of between 1 and 3 mm, and for example of about 1.8 mm, for a weight of less than about 100 g/m2.

The cellulose film and prosthetic fabric may be assembled in a variety of ways to produce the present composite implant.

In embodiments, a 3D fabric is placed on top of the microbial cellulose wet pellicles formed at the surface of a fermentation broth (shown schematically in FIG. 1A). Bacteria are maintained in the culture medium and the pellicle continues to grow into the 3D fabric. This anchors the microbial cellulose wet pellicles to the fabric (shown schematically in FIG. 1B). In embodiments, the pellicle grows into the fabric to a depth of less than 50% the 3D fabric thickness. Purification and depyrogenation processes are then applied on the formed composite material. In embodiments, the cellulose may be further oxidized with periodic acid or nitrogen dioxide.

In other embodiments, cellulose pellicles are harvested at the end of the fermentation of the bacteria. The harvested pellicles are subjected to purification and depyrogenation processes. The cellulose may be further oxidized with periodic acid or nitrogen dioxide. A 3D fabric is placed on top of the microbial cellulose wet pellicles. The anchoring of both materials can be achieved by thermal or chemical melting techniques, such as for example, by using infrared light or thermal or ultraviolet lasers operating in a frequency band such as to produce melting in the cellulose sheet (shown schematically in FIG. 2A). This melting allows the interpenetration of both materials. Such interpenetration may result from capillary absorption of the constituent cellulose fibers in the prosthetic fabric or may be achieved by controlled mechanical compression, such as, for example isostatic compression (shown schematically in FIG. 2B).

In other embodiments, the anchoring of the 3D mesh to the pellicles may be achieved by methods involving (micro)patterning or (micro)printing of the cellulose obtained as described above, in such a way to create grooves in which the 3D mesh can be fully laid. All micropatterning or microprinting techniques known to skilled people may be used, after their adaptation for the present use (Chem. Soc. Rev., 2006, 35, 1287-1304, Eero Kontturi, Tekla Tammelin and Monika Österberg; Chem. Mater. 2001, 13, 3299-3305, Paul Calvert; Journal of Bioactive and Compatible Polymers, Vol. 22, No. 3, 265-280 (2007), A Gupta). The preparation of the cellulose sheets, before the anchoring of the 3D mesh may also include magnetic alignment and patterning of cellulose fibers, on the surface (Sci. Technol. Adv. Mater. 9 (2008), Fumiko Kimura and Tsunehisa Kimura).

As those skilled in the art will appreciate from reading the present disclosure, the cellulose film is intimately linked to the fabric by surface penetration, and cannot be delaminated, so as not to constitute a plane of separation, while at the same time maintaining the porosity open on the other surface of the prosthetic fabric.

The microbial cellulose may be oxidized by periodic acid or by nitrogen dioxide before, after, or during the purification and depyrogenation process. In embodiments, the microbial cellulose may be oxidized when the cellulose is at least partly purified and depyrogenated. The final level of oxidation can be controlled in such a way to produce a resorption time of from several days to several months. The degree of oxidation can be from about 0.1 to about 0.9, in embodiments from about 0.2 to about 0.65.

Other chemical modifications of cellulose for the generation of cellulose derivatives are also within the scope of the present disclosure. Cellulose belong to the family of biodegradable, renewable polymers that provides a broad range of important functional properties, and are thus widely used in industry today. However, some of the inherent properties of these polysaccharides limit their utility in certain applications. Therefore, native cellulose are commonly modified by physical, chemical, enzymatic or genetic means in order to obtain specific functional properties (Richardson, et al., Analytica Chimica Acta, 2003; Kennedy, et al., Cellulose and its Derivatives: Chemistry, Biochemistry and Applications, Ellis Horwood, Chichester, 1985; Guilbot, et al., The Polysaccharides, G. Aspinall (Ed.), Academic Press, New York, 1985). Native cellulose has an intrinsic lack of solubility in water and most organic solvent systems which constitutes a major obstacle for utilizing cellulose in many industrial applications. It may be a goal to chemically derivatize cellulose in such a way to obtain derivatives soluble in organic solvents, for an easier remodeling of the microbial cellulose pellicles, for example.

The chemical modifications of cellulose may be based on reactions of the free hydroxyl groups in the anhydroglucose monomers, resulting in changes in the chemical structure of the glucose units and, ultimately, the production of cellulose derivatives. Usually, these modifications involve esterification or etherification reactions of the hydroxyl groups, in particular with aliphatic halide derivatives.

The composite implant may be easily fixed for surgeries, by any known techniques, among them suturing, stitching, stapling and tacking.

The present composite implants which combine a bacterial cellulose sheet with a 3D prosthetic fabric may advantageously maintain one or more of the original properties of bacterial cellulose sheets (such as, for example, high biocompatibility, extreme hydrophilicity, unique multi-layered three dimensional laminar structures which provide its moisture handling properties, excellent wet strength, high resistance to breakdown under compression, conformability, absence of generation of harmful particles of the cellulose mesh after rubbing against surrounding tissues or erosion at sharp edges of tissues—e.g., sharp edges of bone and cartilage tissues). Bacterial cellulose sheets can have superior mechanical properties compared to other bioresorbable anti-adhesive physical barriers.

It will be understood that various modifications may be made to the embodiments disclosed herein. Thus, those skilled in the art will envision other modifications within the scope and spirit of the disclosure.

The invention claimed is:

1. A method of making a composite implant comprising:
   providing a prosthetic fabric having a first side and a second side separated by a thickness of the prosthetic fabric, wherein the prosthetic fabric is a knit; and
   securing a non-porous film of bacterial cellulose to the first side of the prosthetic fabric, wherein the non-porous film of bacterial cellulose prevents the formation of tissue adhesions on the first side of the prosthetic fabric, and the second side of the prosthetic fabric is porous and open to postsurgical cell colonization.

2. A method of making a composite implant as in claim 1 wherein securing a film of bacterial cellulose to the first side of the prosthetic fabric comprises: contacting the prosthetic fabric with a culture of cellulose-producing bacteria; and culturing cellulose-producing bacteria.

3. A method of making a composite implant as in claim 1 wherein securing a film of bacterial cellulose to the first side of the prosthetic fabric comprises: contacting the prosthetic fabric with a film of bacterial cellulose which has been at least partially melted.

4. A method of making a composite implant as in claim 3 wherein the film of bacterial cellulose has been at least partially melted using infrared light or thermal or ultraviolet lasers.

5. A method of making a composite implant as in claim 3 further comprising applying mechanical pressure to the prosthetic fabric while in contact with the film of bacterial cellulose.

6. A method of making a composite implant as in claim 1 wherein the non-porous film penetrates into the prosthetic fabric to a depth of less than 50% of the thickness of the prosthetic fabric.

7. A method of making a composite implant as in claim 1 wherein the bacterial cellulose comprises oxidized bacterial cellulose.

8. A method of making a composite implant as in claim 1 wherein the prosthetic fabric comprises a three-dimensional knit.

9. A method of making a composite implant as in claim 1 wherein the non-porous film of bacterial cellulose is derived from *Acetobacter xylinum*.

\* \* \* \* \*